United States Patent
Sun et al.

(10) Patent No.: US 12,410,458 B2
(45) Date of Patent: *Sep. 9, 2025

(54) SEMI-CONTINUOUS CULTURE METHODS

(71) Applicant: Mara Renewables Corporation, Dartmouth (CA)

(72) Inventors: Zhiyong Sun, Dartmouth (CA); Michael Milway, Dartmouth (CA); Kevin Berryman, Dartmouth (CA); Mercia Valentine, Dartmouth (CA); Roberto E. Armenta, Dartmouth (CA); Laura Purdue, Dartmouth (CA)

(73) Assignee: Mara Renewables Corporation, Dartmouth (CA)

( * ) Notice: Subject to any disclaimer, the term of this patent is extended or adjusted under 35 U.S.C. 154(b) by 756 days.

This patent is subject to a terminal disclaimer.

(21) Appl. No.: 17/728,833

(22) Filed: Apr. 25, 2022

(65) Prior Publication Data

US 2022/0356506 A1 Nov. 10, 2022

Related U.S. Application Data

(63) Continuation of application No. 16/864,128, filed on Apr. 30, 2020, now Pat. No. 11,345,943, which is a continuation of application No. 14/882,734, filed on Oct. 14, 2015, now Pat. No. 10,676,775.

(60) Provisional application No. 62/064,668, filed on Oct. 16, 2014.

(51) Int. Cl.
| | |
|---|---|
| *C12Q 1/06* | (2006.01) |
| *C12N 1/04* | (2006.01) |
| *C12N 1/12* | (2006.01) |
| *C12N 1/14* | (2006.01) |
| *C12P 7/6409* | (2022.01) |
| *C12P 7/6427* | (2022.01) |
| *C12P 7/6431* | (2022.01) |
| *C12P 7/6432* | (2022.01) |
| *C12P 7/6434* | (2022.01) |
| *C12P 7/6463* | (2022.01) |
| *C12P 7/6472* | (2022.01) |

(52) U.S. Cl.
CPC ........... *C12Q 1/06* (2013.01); *C12N 1/04* (2013.01); *C12N 1/12* (2013.01); *C12N 1/14* (2013.01); *C12P 7/6409* (2013.01); *C12P 7/6427* (2013.01); *C12P 7/6431* (2022.01); *C12P 7/6432* (2022.01); *C12P 7/6434* (2022.01); *C12P 7/6463* (2013.01); *C12P 7/6472* (2013.01)

(58) Field of Classification Search
CPC .............................................. C12P 7/64–6434
See application file for complete search history.

(56) References Cited

U.S. PATENT DOCUMENTS

| | | | |
|---|---|---|---|
| 5,340,594 A | 8/1994 | Barclay | |
| 5,340,742 A | 8/1994 | Barclay | |
| 6,607,900 B2 | 8/2003 | Bailey et al. | |
| 8,163,515 B2 | 4/2012 | Burja et al. | |
| 2009/0117194 A1 | 5/2009 | Burja et al. | |
| 2011/0306102 A1 | 12/2011 | Ratnam et al. | |
| 2012/0244584 A1 | 9/2012 | Zhang et al. | |

FOREIGN PATENT DOCUMENTS

| | | |
|---|---|---|
| CA | 2699406 A1 | 3/2009 |
| CL | 2017000892 A1 | 11/2017 |
| CN | 101981201 A | 2/2011 |
| CN | 102888348 A | 1/2013 |
| JP | 08509355 A | 10/1996 |
| JP | 2010538642 A | 12/2010 |
| JP | 2014507952 A | 4/2014 |
| WO | 9107498 A1 | 5/1991 |
| WO | 2008129358 A2 | 10/2008 |
| WO | 2009035551 A1 | 3/2009 |
| WO | 2009094440 A1 | 7/2009 |
| WO | 2010017243 A1 | 2/2010 |
| WO | 2011155852 A1 | 12/2011 |
| WO | 2012120375 A1 | 9/2012 |
| WO | 2013088407 A1 | 6/2013 |
| WO | 2016059540 | 4/2016 |

OTHER PUBLICATIONS

Marjan Ganjali Dashti, "Repeated Batch Fermentation Biotechnology for the Biosynthesis of Lipid and Gamma-Linolenic Acid by Cunninghamella bainieri 2A1" BioMed Research International vol. 2014, Article ID 831783, 12 pages (Year: 2014).*
AU2023219925, "Second Examination Report", Jun. 13, 2025, 4 pages.
Application No. EP21152366.7, Office Action, Mailed On Jan. 24, 2025, 4 pages.
EP21152366.7, "Office Action", Feb. 7, 2024, 5 pages.
KR2017-7008994 , "Office Action", Aug. 6, 2022, 7 pages.
U.S. Appl. No. 14/882,734 , "Final Office Action", Aug. 7, 2018, 17 pages.
U.S. Appl. No. 14/882,734 , "Non-Final Office Action", Jul. 29, 2019, 12 pages.
U.S. Appl. No. 14/882,734 , "Non-Final Office Action", Nov. 15, 2017, 15 pages.
U.S. Appl. No. 14/882,734 , "Restriction Requirement", Jun. 23, 2017, 7 pages.

(Continued)

*Primary Examiner* — Thane Underdahl
(74) *Attorney, Agent, or Firm* — Kilpatrick Townsend & Stockton LLP (57) ABSTRACT

Provided herein are methods of culturing a microorganism. The methods include providing a container comprising one or more microorganisms in a medium, which has a first carbon to nitrogen ratio; culturing the microorganisms until the culture reaches a threshold indicator; harvesting a portion of the culture while maintaining the majority of the culture in the container; and adding fresh medium comprising a second carbon to nitrogen ratio to the container with the majority of the culture comprising the microorganisms.

20 Claims, 4 Drawing Sheets

(56) References Cited

OTHER PUBLICATIONS

U.S. Appl. No. 16/864,128, "Non-Final Office Action", Jul. 22, 2021, 11 pages.
Ariff et al., "Repeated Fed-Batch Cultivation of Nitrogen-Fixing Bacterium, *Bacillus sphaericus* UPMB10, Using Glycerol as the Carbon Source", Pertanika Journal of Science and Technology, vol. 18, No. 2, Jul. 2010, pp. 365-375.
AU2015332094, "First Examination Report", Jul. 30, 2020, 7 pages.
AU2015332094, "Second Examination Report", Jan. 29, 2021, 3 pages.
Bondioli et al., "Oil Production by the Marine Microalgae *Nannochloropsis* Sp. F&M-M24 and Tetraselmis Suecica F&M-M33", Bioresource Technology, vol. 114, Mar. 10, 2012, pp. 567-572.
BR112017003556-1, "Office Action", Dec. 24, 2019, 8 pages.
Burja et al., "Isolation and Characterization of Polyunsaturated Fatty Acid producing *Thraustochytrium* Species: Screening of Strains and Optimization of Omega-3 Production", Applied Microbiology and Biotechnology, vol. 72, No. 6, 2006, pp. 1161-1169.
CA2,959,860, "Office Action", Feb. 25, 2021, 3 pages.
CA2,959,860, "Office Action", Jan. 4, 2022, 3 pages.
CA2,959,860, "Office Action", Jan. 31, 2020, 4 pages.
Chi et al., "A laboratory study of producing docosahexaenoic acid from biodiesel-waste glycerol by microalgal fermentation", Process Biochemistry vol. 42, 2007, pp. 1537-1545.
Chunsheng et al., "Optimization of Inoculum Draw-Off Volume for Repeated Fed-Batch Fermentation Process", Biotechnology and Bioengineering, vol. 34, 1989, pp. 117-120.
CL201700891, "Office Action", Apr. 17, 2019, 13 pages.
CL201700891, "Office Action", Nov. 28, 2018, 35 pages.
CN201580045740.X, "Office Action", Mar. 19, 2020, 11 pages.
CN201580045740.X, "Office Action", Aug. 6, 2021, 5 pages.
CN201580045740.X, "Office Action", Mar. 30, 2021, 7 pages.
Dashti et al., "Repeated Batch Fermentation Biotechnology for the Biosynthesis of Lipid and Gamma-Linolenic Acid by Cunninghamella Bainieri 2A1", Biomed Research International, vol. 2014, Article ID 831783, Jul. 24, 2014, pp. 1-12.
EP15850279.9, "Extended European Search Report", Mar. 16, 2018, 11 pages.
EP15850279.9, "Office Action", Jan. 7, 2020, 4 pages.
EP15850279.9, "Office Action", May 13, 2020, 4 pages.
EP15850279.9, "Office Action", May 16, 2019, 5 pages.
EP15850279.9, "Office Action", Nov. 23, 2018, 5 pages.
EP21152366.7, "Extended European Search Report", May 25, 2021, 12 pages.
Ethier et al., "Continuous Culture of the Microalgae *Schizochytrium limacinum* on Biodiesel-Derived Crude Glycerol for Producing Docosahexaenoic Acid", Bioresource Technology, vol. 102, No. 1, Jan. 2011, pp. 88-93.
Ganuza et al., "High-Cell-Density Caultivation of *Schizochytrium* Sp. In an Ammonium/Ph-Auxostat Fed-Batch System", Biotechnol Lett, vol. 30, No. 9, 2008, pp. 1559-1564.
Ganuza et al., "Lipid Accumulation in Schizochytrium G13/2S Produced in Continuous Culture", Appl Microbiol Biotechnol, vol. 76, No. 5, Oct. 2007, pp. 985-990.
Han et al., "Enhanced Lipid Productivity of Chlorella Pyrenoidosa Through the Culture Strategy of Semi-Continuous Cultivation with Nitrogen Limitation and PH Control by CO2", Bioresource Technology, vol. 136, Mar. 14, 2013, pp. 418-424.
IL250275, "Office Action", Dec. 24, 2019, 8 pages.
Immelman et al., "Effect of C:N Ratio on Gamma-linolenic Acid Production by Mucor circinelloides Grown on Acetic Acid", Systematic and Applied Microbiology, vol. 20, Issue 1, Jan. 1997, pp. 158-164.
IN201717003899, "First Examination Report", Sep. 22, 2021, 10 pages.
JP2017-513131, "Office Action", Aug. 6, 2019, 13 pages.
JP2017-513131, "Office Action", Jun. 2, 2020, 8 pages.
KR2017-7008994, "Office Action", Feb. 16, 2022, 9 pages.
Leyland et al., "Are Thraustochytrids Algae?", Fungal Biology vol. 121, 2017, pp. 835-840.
Longobardi, "Fed-Batch Versus Batch Fermentation", Bioprocess Engineering, vol. 10, Nos. 5-6, May 1994, pp. 185-194.
Ma et al., "The Fermenter High Density Heterotrophic Culture of Chlorella", Guangdong Chemical Industry, vol. 40, No. 4, Feb. 28, 2013, pp. 15-17.
Meng et al., "Biodiesel Production From Oleaginous Microorganisms", Renewable Energy, vol. 34, No. 1, Jan. 2009, pp. 1-5.
MX/A/2017/002234, "Office Action", Sep. 15, 2020, 4 pages.
PCT/IB2015/057807, "International Preliminary Report on Patentability", Apr. 27, 2017, 8 pages.
PCT/IB2015/057807, "International Search Report and Written Opinion", Jan. 14, 2016, 9 pages.
Pedro et al., "Marine Microalgae Selection and Culture Conditions Optimization for Biodiesel Production", Bioresource Technology, vol. 134, Feb. 22, 2013, pp. 353-361.
Qu et al., "Batch, Fed-Batch and Repeated Fed-Batch Fermentation Processes of the Marine *Thraustochytrid schizochytrium* Sp. For Producing Docosahexaenoic Acid", Bioprocess and Biosystems Engineering, vol. 36, No. 12, May 15, 2013, pp. 1905-1912.
Raghukumar, "Thraustochytrid Marine Protists: Production of PUFAs and Other Emerging Technologies", Marine Biotechnology, vol. 10, No. 6, Aug. 20, 2008, pp. 631-640.
Raimondi et al., "Getting Lipids from Glycerol: New Perspectives on Biotechnological Exploitation of Candida Freyschussii", Microbial Cell Factories, vol. 13, No. 83, Jun. 7, 2014, pp. 1-11.
Rasheva et al., "Lipid Production by Monascus Purpureus Albino Strain", Journal of Biotechnology, vol. 56, No. 3, Available Online at: https://www.sciencedirect.com/science/article/abs/pii/S0168165697001120?via%3Dihub, Aug. 28, 1997, pp. 217-224.
Rodolfi et al., "Microalgae for Oil: Strain Selection, Induction of Lipid Synthesis and Outdoor Mass Cultivation in a Low-Cost Photobioreactor", Biotechnology and Bioengineering, vol. 102, No. 1, Jan. 1, 2009, pp. 100-112.
Roux et al., "Mucor—A Source of Cocoa Butter and Gamma-Linolenic Acid", World Journal of Microbiology & Biotechnology, vol. 10, No. 4, Jul. 1994, pp. 417-422.
Sattur et al., "Production of Microbial Lipids: I. Development of a Mathematical Model", Biotechnology and Bioengineering, vol. 34, No. 6, 1989, pp. 863-867.
Sattur et al., "Production of Microbial Lipids: III. Influence of C/N Ratio-Experimental Observations", Biotechnology and Bioengineering, vol. 34, Dec. 28, 1989, pp. 872-874.
Shene et al., "Microbial Oils and Fatty Acids: Effect of Carbon Source on Docosahexaenoic Acid (C22:6 N-3, DHA) Production By Thraustochytrid Strains", Journal of Soil Science and Plant Nutrition, vol. 10, No. 3, 2010, pp. 207-216.
Shene et al., "Production of Lipids and Docosahexasaenoic Acid (DHA) by a Native Thraustochytrium Strain", European Journal of Lipid Science and Technology, vol. 115, No. 8, May 31, 2013, pp. 890-900.
Wen et al., "Continuous Cultivation of the Diatom Nitzschia Laevis for Eicosapentaenoic Acid Production: Physiological Study and Process Optimization", Biotechnology Progr, vol. 18, No. 1, 2002, pp. 21-28.
Yaguchi et al., "Production of High Yields of Docosahexaenoic Acid by *Schizochytrium* sp. Strain SR2", Jaocs vol. 74, No. 11, Nov. 1997, pp. 1431-1434.
Yokochi et al., "Optimization of Docosahexaenoic Acid Productions by Schizochytrium Limacinum SR21", Applied Microbiology and Biotechnology, vol. 49, Issue 1, Jan. 1998, pp. 72-76.
Yokochi et al., "Studies on Production of Lipids in Fungi (XXII), Production of γ-Linolenic Acid by Genus *Mortierella*", Petrochemistry, vol. 38, No. 12, 1989, pp. 1007-1015.
NZ728653, "First Examination Report", Sep. 9, 2022, 5 pages.
NZ728653, "Second Examination Report", Feb. 28, 2023, 4 pages.
AU2023219925, "First Examination Report", Feb. 20, 2025, 5 pages.

(56) References Cited

OTHER PUBLICATIONS

AU2021218000, "First Examination Report", Feb. 24, 2023, 4 pages.
BR112017003556-1, "Office Action", May 2, 2023, 6 pages.

* cited by examiner

SEMI-CONTINUOUS CULTURE METHODS

CROSS-REFERENCE TO RELATED APPLICATION

This application is a continuation of U.S. patent application Ser. No. 16/864,128 filed Apr. 30, 2020, which is a continuation of U.S. patent application Ser. No. 14/882,734, filed Oct. 14, 2015 (now U.S. Pat. No. 10,676,775), which claims priority to U.S. Provisional Application No. 62/064,668, filed Oct. 16, 2014, which are incorporated herein by reference in their entireties.

BACKGROUND

Heterotrophic fermentations of microorganisms including Thraustochytrid species are efficient ways of generating high value oil and biomass products. Under certain cultivation conditions, microorganisms synthesize intracellular oil, which can be extracted and used to produce biofuel (biodiesel, bio-jetfuel, and the like) and nutritional lipids (polyunsaturated fatty acids, e.g. DHA, EPA, DPA). The biomass of microorganisms such as Thraustochytrid species is also of great nutritional value due to the high PUFA and protein content and can be used as nutritional supplement for animal feed.

Microorganism fermentation processes are carried out mostly in batch or fed-batch processes. Batch processes typically involve a closed system culture in which cells are grown in a fixed volume of nutrient culture medium under specific conditions (e.g., nutrients, temperature, pressure, and the like) to a certain density in a fermenter, harvested and processed as a batch. In typical fed-batch processes, one or more nutrients are fed or supplied to a fermenter, in which they remain until the end of the culture process. Fed-batch culture processes can be superior to batch culture processes when controlling concentrations of a nutrient (or nutrients) affects the yield or activity of a desired product. Such fermentation processes are typically comprised of two cultivation stages, a cell proliferation stage, during which all necessary nutrients are available for unlimited culture growth, followed by an oil accumulation stage, during which a key growth nutrient (typically nitrogen) is purposely limited in the medium while excessive carbon nutrient is provided and channeled into oil synthesis. When the target cell concentration and oil content is reached, the fermentation process is stopped and oil-rich biomass is harvested. The fermenter vessel then must be cleaned, sterilized and re-batched with fresh medium, and a seed train needs to be ready to inoculate the production vessel again (e.g., a "turnaround" operation between batch/fed-batch fermentations). Such a turnaround operation is often time and energy consuming and limits the total available operating hours of the production vessel for an established production process. Alternatively, microorganisms can be cultured using continuous methods where fresh medium is continuously added to the fermenter, while culture liquid is continuously removed to keep the culture volume constant. Continuous culture processes can be used to maintain the microorganism at a specific growth rate or physiological steady state, but can be difficult to maintain without disruption and are typically used for research purposes, as fed-batch or batch cultures tend provide better results (e.g., higher oil yield) and are easier to use for large scale production purposes.

BRIEF SUMMARY

Provided herein are optimized methods of culturing a microorganism and methods of producing oil and promoting prolonged biomass productivity using a semi-continuous process. The methods include providing a container comprising one or more microorganisms in a medium comprising a first carbon to nitrogen ratio, culturing the microorganisms until the culture reaches a threshold indicator, harvesting a portion of the culture while maintaining the majority of the culture in the container, and adding fresh medium comprising a second carbon to nitrogen ratio to the container comprising the majority of the culture comprising the microorganisms.

DETAILED DESCRIPTION

Methods of cultivating microorganisms and methods of producing oil by a semi-continuous process are provided herein. The methods result in higher overall volumetric biomass and oil productivity as compared to typical batch, continuous and fed-batch processes. Briefly, microorganisms are provided in an initial culture (e.g., seed culture) and are grown using a fed-batch fermentation process to a certain threshold parameter, e.g., high cell concentration and/or high oil content, at which point the nitrogen source is limited or exhausted in the medium, the carbon source is zero or near zero, and the biomass/oil productivity are within their maximum range for the given microorganism. A certain volume of the culture broth is harvested (e.g., 10% of the working volume), and the same volume of fresh medium containing a predefined concentration of carbon and nitrogen nutrients as well as all other necessary mineral nutrients is added to the fermenter. The carbon and nitrogen ratio used in the feeding medium is in order to obtain and maintain high oil content in the culture. The cultivation continues with the culture developing additional biomass and oil using the newly provided medium. The culture is grown until a threshold parameter is reached (e.g., carbon concentration is reduced to zero or near zero), and the partial broth harvest and fresh medium supply cycle is repeated. Using such a process, high density biomass containing high oil content can be produced and harvested in a semi-continuous manner, and the total duration of the process is much longer than any batch or fed-batch mode cultivation of such microorganisms. The semi-continuous harvesting of high density biomass with high oil content significantly reduces fermenter turnaround time, minimizes the need for fermenter vessel turnaround procedure and sterilization procedure therefore lowering the operation cost, and can result in very high overall volumetric productivity of biomass and oil, far exceeding what can be achieved by typical batch, continuous or fed-batch fermentation methods.

Microorganisms

The methods described herein include extracting lipids from a population of microorganisms. The population of microorganisms described herein can be algae (e.g., microalgae), fungi (including yeast), bacteria, or protists. Optionally, the microorganism includes *Thraustochytrids* of the order *Thraustochytriales*, more specifically *Thraustochytriales* of the genus *Thraustochytrium*. Optionally, the population of microorganisms includes *Thraustochytriales* as described in U.S. Pat. Nos. 5,340,594 and 5,340,742, which are incorporated herein by reference in their entireties. The microorganism can be a *Thraustochytrium* species, such as the *Thraustochytrium* species deposited as ATCC Accession No. PTA-6245 (i.e., ONC-T18) as described in U.S. Pat. No. 8,163,515, which is incorporated by reference herein in its entirety. Thus, the microorganism can have an 18s rRNA sequence that is at least 95%, 96%, 97%, 98%, 99%, 99.1%, 99.2%, 99.3%, 99.4%, 99.5%, 99.6%, 99.7%, 99.8%, 99.9% or more (e.g., including 100%) identical to SEQ ID NO: 1.

The microorganisms for use in the methods described herein can produce a variety of lipid compounds. As used herein, the term lipid includes phospholipids, free fatty acids, esters of fatty acids, triacylglycerols, sterols and sterol esters, carotenoids, xanthophyls (e.g., oxycarotenoids), hydrocarbons, and other lipids known to one of ordinary skill in the art. Optionally, the lipid compounds include unsaturated lipids. The unsaturated lipids can include polyunsaturated lipids (i.e., lipids containing at least 2 unsaturated carbon-carbon bonds, e.g., double bonds) or highly unsaturated lipids (i.e., lipids containing 4 or more unsaturated carbon-carbon bonds). Examples of unsaturated lipids include omega-3 and/or omega-6 polyunsaturated fatty acids, such as docosahexaenoic acid (i.e., DHA), eicosapentaenoic acid (i.e., EPA), and other naturally occurring unsaturated, polyunsaturated and highly unsaturated compounds.

Processes

Provided herein is method of culturing a microorganism. The method includes providing a container of one or more microorganisms in a medium, having a first carbon to nitrogen ratio; culturing the microorganisms until the culture reaches a threshold indicator; harvesting a portion of the culture while maintaining the majority of the culture in the container; and adding fresh medium having a second carbon to nitrogen ratio to the container containing the majority of the culture with the microorganisms.

The methods are applicable to large-scale fermentation as well as small-scale fermentation. Large-scale fermentation, as used herein, refers to fermentation in a fermenter that is at least approximately 1,000 L in volumetric capacity (i.e., working volume), leaving adequate room for headspace. Small-scale fermentation refers generally to fermentation in a fermenter that is generally no more than approximately 100 L in volumetric capacity, such as 5 L, 10 L, 50 L or 100 L. A demonstrated advantage of the present fed-batch fermentation process is that it may be utilized for the production of oil at the 5-10 L fermenter scale and is scalable to any volume, for example, 100 L, 150 L, 250 L, 500 L, 1000 L or more, without limitation.

As discussed throughout, provided herein is a method of culturing a microorganism that includes providing a container with one or more microorganisms in a medium comprising a first carbon to nitrogen ratio. Typically, media include carbon sources at a concentration of about 5 g/L to about 200 g/L and have a C:N (carbon to nitrogen) molar ratio between about 1:1 and about 40:1. In the provided methods, the first carbon to nitrogen molar ratio is from 30:1 to 60:1. Optionally, the first carbon to nitrogen molar ratio is from 40:1 to 50:1. As discussed in more detail throughout, carbon sources include, but are not limited to, fatty acids, lipids, glycerols, triglycerols, carbohydrates, polyols, and amino sugars. Optionally, the carbon source is glucose, fructose, or glycerol. As discussed in more detail throughout, nitrogen sources include, but are not limited to, ammonium solutions, ammonium or amine salts, peptone, tryptone, yeast extract, malt extract, fish meal, sodium glutamate, soy extract, casamino acids and distiller grains. Optionally, the nitrogen source is ammonium sulfate.

The provided methods include culturing the microorganisms until the culture reaches a threshold indicator. As used herein, the term parameter refers to an indicator or variable used to monitor and control the progress of a microorganism culture. Such parameters include, but are not limited to, optical density (OD), cell concentration, carbon dioxide production rate, pH, dissolved oxygen (DO), time, concentration of nutrient in culture medium, accumulation of metabolic by-products, temperature, biomass productivity, and oil productivity. Any suitable parameter or combination of parameters is contemplated for use as would be understood by a person of ordinary skill in the art and based upon the guidance provided herein. Optionally, the parameter is a concentration of nutrient(s) in the culture medium. Suitable nutrients that can be measured in the culture medium include, but are not limited to, carbon and nitrogen.

The provided methods include harvesting a portion of the culture while maintaining the majority of the culture in the container. In the methods, the portion harvested comprises from about 5 to about 20% of the culture. Optionally, the portion harvested comprises about 10% of the culture.

The provided methods also include adding fresh medium comprising a second carbon to nitrogen ratio to the container comprising the majority of the culture with the microorganisms. As used herein, the term majority means that 50% or more of the culture comprising the microorganisms remains in the container while the remaining portion of the culture is harvested. In the provided methods, the second carbon nitrogen ratio is typically higher than the first carbon nitrogen ratio. The second carbon to nitrogen ratio can range from about 60:1 to about 95:1. Optionally, the second carbon to nitrogen ratio is from about 80:1 to about 90:1. As discussed in more detail throughout, carbon sources include, but are not limited to, fatty acids, lipids, glycerols, triglycerols, carbohydrates, polyols, and amino sugars. Optionally, the carbon source is glucose, fructose, or glycerol. As discussed in more detail throughout, nitrogen sources include, but are not limited to, ammonium solutions, ammonium or amine salts, peptone, tryptone, yeast extract, malt extract, fish meal, sodium glutamate, soy extract, casamino acids and distiller grains. Optionally, the nitrogen source is ammonium sulfate.

The provided methods optionally include repeating the steps of (i) culturing the microorganisms until the culture reaches a threshold indicator; (ii) harvesting a portion of the culture while maintaining the majority of the culture in the container; and (iii) adding fresh medium with the second carbon to nitrogen ratio to the container comprising the majority of the culture comprising the microorganisms. In this way, the provided methods advantageously allow for the culture to be maintained over a longer period of time during which the culture maintains a high level of biomass and/or oil productivity. Optionally, the culture is maintained for a period of hours, days, weeks or months. Optionally, the culture is maintained for at least 150 to 500 hours. For example, the culture can be maintained for at least 250 hours. Optionally, the culture is maintained for one, two, three, four, or five weeks.

The provided methods allow for the culture to be maintained at a high level of biomass productivity. As used herein, the term "high level of biomass productivity" refers to a level that is higher than the average biomass productivity for a given microorganism. Typically, average productivity levels tend to be in the range of 40 g/L-d or below, i.e., from 0 g/L-d to about 40 g/L-d but may vary depending on the microorganism. Optionally, the biomass productivity comprises 60 g/L-d to 180 g/L-d. Optionally, the biomass productivity comprises 80 g/L-d to 130 g/L-d. Optionally, the biomass productivity comprises 90 g/L-d to 100 g/L-d. As used herein, the term "high"

The provided methods also allow for the culture to be maintained at a high level of oil productivity. As used herein, the term "high level of oil productivity" refers to a level that is higher than the average oil productivity for a given microorganism. Typically, average productivity levels tend to be in the range of 25 g/L-d or below, i.e., from 0 g/L-d to about 25 g/L-d but may vary depending on the microorganism. Optionally, the oil productivity comprises 35 g/L-d to 130 g/L-d. Optionally, the oil productivity comprises 60 g/L-d to 90 g/L-d. Optionally, the oil productivity comprises 70 g/L-d to 80 g/L-d. Thus, for example, the culture of microorganisms comprises a biomass comprising 60% to 85% oil. Optionally, the culture of microorganisms comprises a biomass comprising 65% to 75% oil.

The terms high, higher, increases, elevate, or elevation refer to increases above a control. The terms low, lower, reduces, or reduction refer to any decrease below control levels. By way of example, control levels are levels of biomass and/or oil productivity grown under batch, fed-batch, or continuous conditions. The provided methods provide for biomass and/or oil productivity levels that are higher than levels when the same microorganisms are grown using a different process, e.g., a batch, fed-batch, or continuous process. Biomass productivity levels can be determined, for example, by assuming a 24-hour turnaround time to be included to the total process time, the overall biomass (X) productivity at any given time point of the process can be calculated as: X (gram)/Culture Volume (liter)/Time (hour)×24 (hours/day) with the final unit being g/L-day. The overall oil productivity at any given time point can be similarly calculated as: Oil (gram)/Culture Volume (liter)/Time (hour)×24 (hours/day).

Fermentation

The provided methods include or can be used in conjunction with additional steps for culturing microorganisms according to methods known in the art. For example, a Thraustochytrid, e.g., a *Thraustochytrium* sp., can be cultivated according to methods described in U.S. Patent Publications 2009/0117194 or 2012/0244584, which are herein incorporated by reference in their entireties for each step of the methods or composition used therein. Microorganisms are grown in a growth medium (also known as "culture medium"). Any of a variety of medium can be suitable for use in culturing the microorganisms described herein. Optionally, the medium supplies various nutritional components, including a carbon source and a nitrogen source, for the microorganism.

Medium for Thraustochytrid culture can include any of a variety of carbon sources. Examples of carbon sources include fatty acids, lipids, glycerols, triglycerols, carbohydrates, polyols, amino sugars, and any kind of biomass or waste stream. Fatty acids include, for example, oleic acid. Carbohydrates include, but are not limited to, glucose, cellulose, hemicellulose, fructose, dextrose, xylose, lactulose, galactose, maltotriose, maltose, lactose, glycogen, gelatin, starch (corn or wheat), acetate, m-inositol (e.g., derived from corn steep liquor), galacturonic acid (e.g., derived from pectin), L-fucose (e.g., derived from galactose), gentiobiose, glucosamine, alpha-D-glucose-1-phosphate (e.g., derived from glucose), cellobiose, dextrin, alpha-cyclodextrin (e.g., derived from starch), and sucrose (e.g., from molasses). Polyols include, but are not limited to, maltitol, erythritol, and adonitol. Amino sugars include, but are not limited to, N-acetyl-D-galactosamine, N-acetyl-D-glucosamine, and N-acetyl-beta-D-mannosamine. Optionally, the carbon source is glucose. As noted above, in the provided methods, the carbon source is provided at a high concentration, e.g., at least 200 g/L.

Optionally, the microorganisms provided herein are cultivated under conditions that increase biomass and/or production of a compound of interest (e.g., oil or total fatty acid (TFA) content). *Thraustochytrids*, for example, are typically cultured in saline medium. Optionally, *Thraustochytrids* can be cultured in medium having a salt concentration from about 0.5 g/L to about 50.0 g/L. Optionally, *Thraustochytrids* are cultured in medium having a salt concentration from about 0.5 g/L to about 35 g/L (e.g., from about 18 g/L to about 35 g/L). Optionally, the *Thraustochytrids* described herein can be grown in low salt conditions. For example, the *Thraustochytrids* can be cultured in a medium having a salt concentration from about 0.5 g/L to about 20 g/L (e.g., from about 0.5 g/L to about 15 g/L). The culture medium optionally includes NaCl. Optionally, the medium includes natural or artificial sea salt and/or artificial seawater.

The culture medium can include non-chloride-containing sodium salts as a source of sodium. Examples of non-chloride sodium salts suitable for use in accordance with the present methods include, but are not limited to, soda ash (a mixture of sodium carbonate and sodium oxide), sodium carbonate, sodium bicarbonate, sodium sulfate, and mixtures thereof. See, e.g., U.S. Pat. Nos. 5,340,742 and 6,607,900, the entire contents of each of which are incorporated by reference herein. A significant portion of the total sodium, for example, can be supplied by non-chloride salts such that less than about 100%, 75%, 50%, or 25% of the total sodium in culture medium is supplied by sodium chloride.

Optionally, the culture medium has chloride concentrations of less than about 3 g/L, 500 mg/L, 250 mg/L, or 120 mg/L. For example, culture medium for use in the provided methods can have chloride concentrations of between and including about 60 mg/L and 120 mg/L.

Medium for *Thraustochytrids* culture can include any of a variety of nitrogen sources. Exemplary nitrogen sources include ammonium solutions (e.g., $NH_4$ in $H_2O$), ammonium or amine salts (e.g., $(NH_4)_2SO_4$, $(NH_4)_3PO_4$, $NH_4NO_3$, $NH_4OOCH_2CH_3$ ($NH_4Ac$)), peptone, tryptone, yeast extract, malt extract, fish meal, sodium glutamate, soy extract, casamino acids and distiller grains. Concentrations of nitrogen sources in suitable medium typically range between and including about 1 g/L and about 25 g/L.

The medium optionally includes a phosphate, such as potassium phosphate or sodium-phosphate. Inorganic salts and trace nutrients in medium can include ammonium sulfate, sodium bicarbonate, sodium orthovanadate, potassium chromate, sodium molybdate, selenous acid, nickel sulfate, copper sulfate, zinc sulfate, cobalt chloride, iron chloride, manganese chloride calcium chloride, and EDTA. Vitamins such as pyridoxine hydrochloride, thiamine hydrochloride, calcium pantothenate, p-aminobenzoic acid, riboflavin, nicotinic acid, biotin, folic acid and vitamin B12 can be included.

The pH of the medium can be adjusted to between and including 3.0 and 10.0 using acid or base, where appropriate, and/or using the nitrogen source. Optionally, the medium is adjusted to a low pH as defined above. The medium can be sterilized.

Generally a medium used for culture of a microorganism is a liquid medium. However, the medium used for culture of a microorganism can be a solid medium. In addition to carbon and nitrogen sources as discussed herein, a solid medium can contain one or more components (e.g., agar or agarose) that provide structural support and/or allow the medium to be in solid form.

Cells can be cultivated over a period of time. Optionally, the cells are cultured for anywhere from 1 day to 60 days. Optionally, the culture is maintained for a period of hours, days, weeks or months. Optionally, the culture is maintained for at least 150 to 500 hours. Optionally, the culture is maintained for at least 250 hours. Optionally, the culture is maintained for one, two, three, four, or five weeks. Cultivation is optionally carried out at temperatures from about 4° C. to about 30° C., e.g., from about 18° C. to about 28° C. Cultivation can include aeration-shaking culture, shaking culture, stationary culture, batch culture, semi-continuous culture, continuous culture, rolling batch culture, wave culture, or the like. Cultivation can be performed using a conventional agitation-fermenter, a bubble column fermenter (batch or continuous cultures), an airlift fermenter, a wave fermenter, and the like.

Cultures can be aerated by one or more of a variety of methods, including shaking. Optionally, shaking ranges from about 100 rpm to about 1000 rpm, e.g., from about 350 rpm to about 600 rpm or from about 100 to about 450 rpm. Optionally, the cultures are aerated using different shaking speeds during biomass-producing phases and during lipid-producing phases. Alternatively or additionally, shaking speeds can vary depending on the type of culture vessel (e.g., shape or size of flask).

The production of desirable lipids can be enhanced by culturing cells according to methods that involve a shift of one or more culture conditions in order to obtain higher quantities of desirable compounds. Optionally, cells are cultured first under conditions that maximize biomass, followed by a shift of one or more culture conditions to conditions that favor lipid productivity. Conditions that are shifted can include oxygen concentration, C:N ratio, temperature, and combinations thereof. Optionally, a two-stage culture is performed in which a first stage favors biomass production (e.g., using conditions of high oxygen (e.g., generally or relative to the second stage), low C:N ratio, and ambient temperature), followed by a second stage that favors lipid production (e.g., in which oxygen is decreased, C:N ratio is increased, and temperature is decreased, as compared to the first stage). In contrast to previously described methods, the provided methods allow for maintaining the culture for a prolonged time under conditions at high levels of oil or lipid production.

Pasteurization

Optionally, the resulting biomass is pasteurized to inactivate undesirable substances present in the biomass. For example, the biomass can be pasteurized to inactivate compound degrading substances. The biomass can be present in the fermentation medium or isolated from the fermentation medium for the pasteurization step. The pasteurization step can be performed by heating the biomass and/or fermentation medium to an elevated temperature. For example, the biomass and/or fermentation medium can be heated to a temperature from about 50° C. to about 95° C. (e.g., from about 55° C. to about 90° C. or from about 65° C. to about 80° C.). Optionally, the biomass and/or fermentation medium can be heated from about 30 minutes to about 120 minutes (e.g., from about 45 minutes to about 90 minutes, or from about 55 minutes to about 75 minutes). The pasteurization can be performed using a suitable heating means as known to those of skill in the art, such as by direct steam injection.

Optionally, no pasteurization step is performed. Stated differently, the method taught herein optionally lacks a pasteurization step.

Harvesting and Washing

Optionally, the biomass can be harvested according to a variety of methods including those currently known to one skilled in the art. For example, the biomass can be collected from the fermentation medium using, for example, centrifugation (e.g., solid-ejecting centrifuges) or filtration (e.g., cross-flow filtration), optionally with a precipitation agent for the accelerated collection of cellular biomass (e.g., sodium phosphate or calcium chloride).

Optionally, the biomass is washed with water. Optionally, the biomass can be concentrated up to about 20% solids. For example, the biomass can be concentrated to about 5% to about 20% solids, from about 7.5% to about 15% solids, or from about solids to about 20% solids, or any percentage within the recited ranges. Optionally, the biomass can be concentrated to about 20% solids or less, about 19% solids or less, about 18% solids or less, about 17% solids or less, about 16% solids or less, about 15% solids or less, about 14% solids or less, about 13% solids or less, about 12% solids or less, about 11% solids or less, about 10% solids or less, about 9% solids or less, about 8% solids or less, about 7% solids or less, about 6% solids or less, about 5% solids or less, about 4% solids or less, about 3% solids or less, about 2% solids or less, or about 1% solids or less.

Isolation and Extraction

The provided methods, optionally, include isolating the polyunsaturated fatty acids from the biomass or microorganisms using a variety of methods, including those currently known to one of skill in the art. For example, methods of isolating polyunsaturated fatty acids are described in U.S. Pat. No. 8,163,515, which is incorporated by reference herein in its entirety. Optionally, the medium is not sterilized prior to isolation of the polyunsaturated fatty acids. Optionally, sterilization comprises an increase in temperature. Optionally, the polyunsaturated fatty acids produced by the microorganisms and isolated from the provided methods are medium chain fatty acids. Optionally, the one or more polyunsaturated fatty acids are selected from the group consisting of alpha linolenic acid, arachidonic acid, docosahexaenoic acid, docosapentaenoic acid, eicosapentaenoic acid, gamma-linolenic acid, linoleic acid, linolenic acid, and combinations thereof.

Products

Oil including polyunsaturated fatty acids (PUFAs) and other lipids produced according to the method described herein can be utilized in any of a variety of applications exploiting their biological, nutritional, or chemical properties. Thus, the provided methods optionally include isolating oil from the harvested culture. Optionally, the oil is used to produce fuel, e.g., biofuel. Optionally, the oil can be used in pharmaceuticals, food supplements, animal feed additives, cosmetics, and the like. Lipids produced according to the methods described herein can also be used as intermediates in the production of other compounds.

By way of example, the oil produced by the microorganisms cultured using the provided methods can comprise fatty acids. Optionally, the fatty acids are selected from the group consisting of alpha linolenic acid, arachidonic acid, docosahexaenoic acid, docosapentaenoic acid, eicosapentaenoic acid, gamma-linolenic acid, linoleic acid, linolenic acid, and combinations thereof. Optionally, the oil comprises triglycerides. Optionally, the oil comprises fatty acids selected from the group consisting of palmitic acid (C16:0), myristic acid (C14:0), palmitoleic acid (C16:1(n−7)), cis-vaccenic acid (C18:1(n−7)), docosapentaenoic acid (C22:5(n−6)), docosahexaenoic acid (C22:6(n−3)), and combinations thereof. Optionally, the concentration of docosahexaenoic acid in the isolated fatty acids is 20% or less of the total fatty acid concentration.

Optionally, the lipids produced according to the methods described herein can be incorporated into a final product (e.g., a food or feed supplement, an infant formula, a pharmaceutical, a fuel, etc.) Suitable food or feed supplements into which the lipids can be incorporated include beverages such as milk, water, sports drinks, energy drinks, teas, and juices; confections such as candies, jellies, and biscuits; fat-containing foods and beverages such as dairy products; processed food products such as soft rice (or porridge); infant formulae; breakfast cereals; or the like. Optionally, one or more produced lipids can be incorporated into a dietary supplement, such as, for example, a vitamin or multivitamin. Optionally, a lipid produced according to the method described herein can be included in a dietary supplement and optionally can be directly incorporated into a component of food or feed (e.g., a food supplement).

Examples of feedstuffs into which lipids produced by the methods described herein can be incorporated include pet foods such as cat foods; dog foods and the like; feeds for aquarium fish, cultured fish or crustaceans, etc.; feed for farm-raised animals (including livestock and fish or crustaceans raised in aquaculture). Food or feed material into which the lipids produced according to the methods described herein can be incorporated is preferably palatable to the organism which is the intended recipient. This food or feed material can have any physical properties currently known for a food material (e.g., solid, liquid, soft).

Optionally, one or more of the produced compounds (e.g., PUFA) can be incorporated into a nutraceutical or pharmaceutical. Examples of such a nutraceuticals or pharmaceuticals include various types of tablets, capsules, drinkable agents, etc. Optionally, the nutraceutical or pharmaceutical is suitable for topical application. Dosage forms can include, for example, capsules, oils, granula, granula subtilae, pulveres, tabellae, pilulae, trochisci, or the like.

The oil or lipids produced according to the methods described herein can be incorporated into products as described herein in combination with any of a variety of other agents. For instance, such compounds can be combined with one or more binders or fillers, chelating agents, pigments, salts, surfactants, moisturizers, viscosity modifiers, thickeners, emollients, fragrances, preservatives, etc., or any combination thereof.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

As used throughout, ranges (e.g., 1-10) and references to about a given value (e.g., about 1 or about 10) includes the recited value or values (e.g., 1 and/or 10)

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

Semi-Continuous Fermentation for Production of Biomass and Oil

In the field of microbial oil production, heterotrophic dark fermentation is generally considered superior to auto phototrophic microbial cultivation in terms of process efficiency and product yield. However it is often hindered by higher fixed capital cost (the cost of constructing a vessel-based fermentation plant is generally much higher than the capital cost of open-pond and raceway type cultivation system). Using such semi-continuous production processes as described herein, higher overall productivity can be achieved with lowered operating cost (minimizing production fermenter vessel turnaround procedure and vessel sterilization procedure). This means better utilization of fixed capital investment (fermenters and associated capital equipment) and higher annual production capacity.

Figure 1:
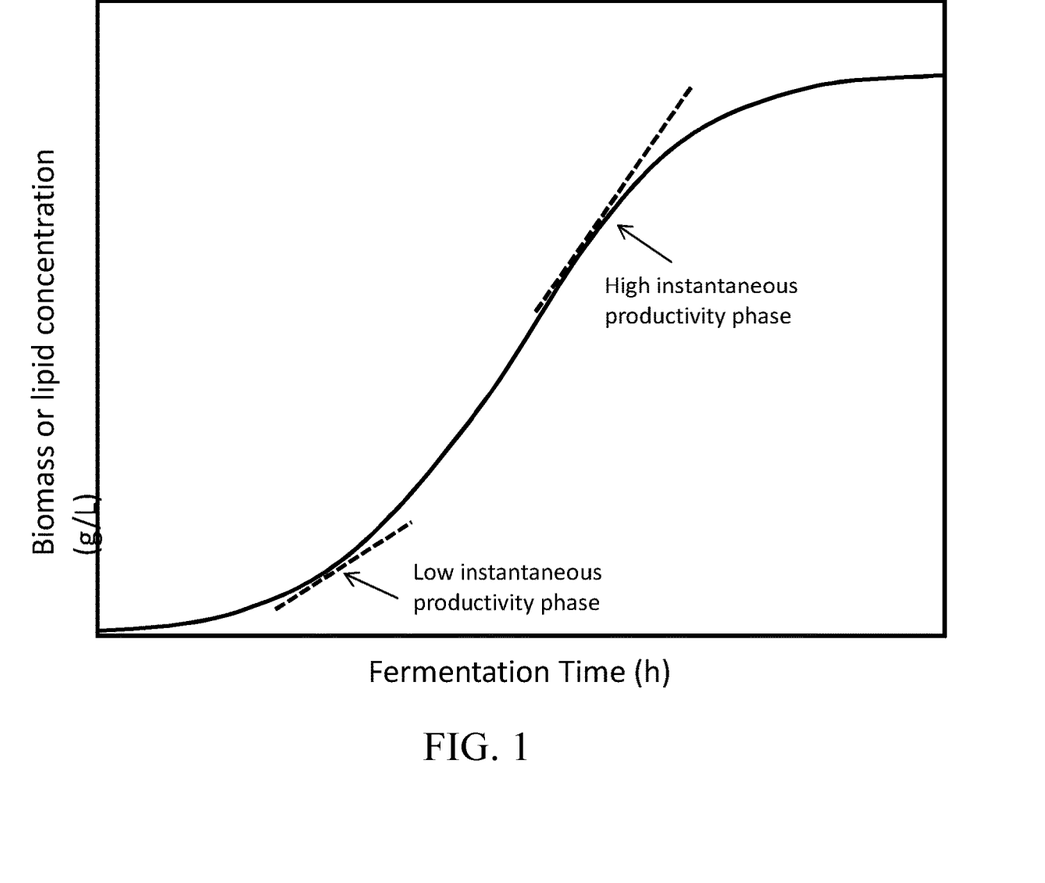
FIG. 1 is a graph illustrating a typical microbial S-shaped growth curve. The instantaneous biomass/oil productivity is at its highest level later in the process but before the culture reaches stationary phase, which can be indicated by the steepest slope on the S-curve.

During fed-batch microorganism cultivation, the culture cell/oil concentration follows a typical microbial S-shaped growth curve (FIG. 1), and the instantaneous biomass/oil productivity is at its highest level later in the process but before the culture reaches stationary phase, which can be indicated by the steepest slope on the S-curve (FIG. 1). However, a typical fed-batch cultivation is stopped shortly after the culture passed the high instantaneous productivity phase, and the overall productivity cannot be very high because the culture had spent much of the process time going through the lower instantaneous productivity phase before the high instantaneous productivity phase can be reached. The semi-continuous process takes advantage of the culture's ability to grow and synthesize oil during the high instantaneous productivity phase by repeatedly harvesting a certain volume of broth at high concentration while supplying newly balanced medium to allow the culture to generate biomass and oil repeatedly at the higher rate.

Figure 2:
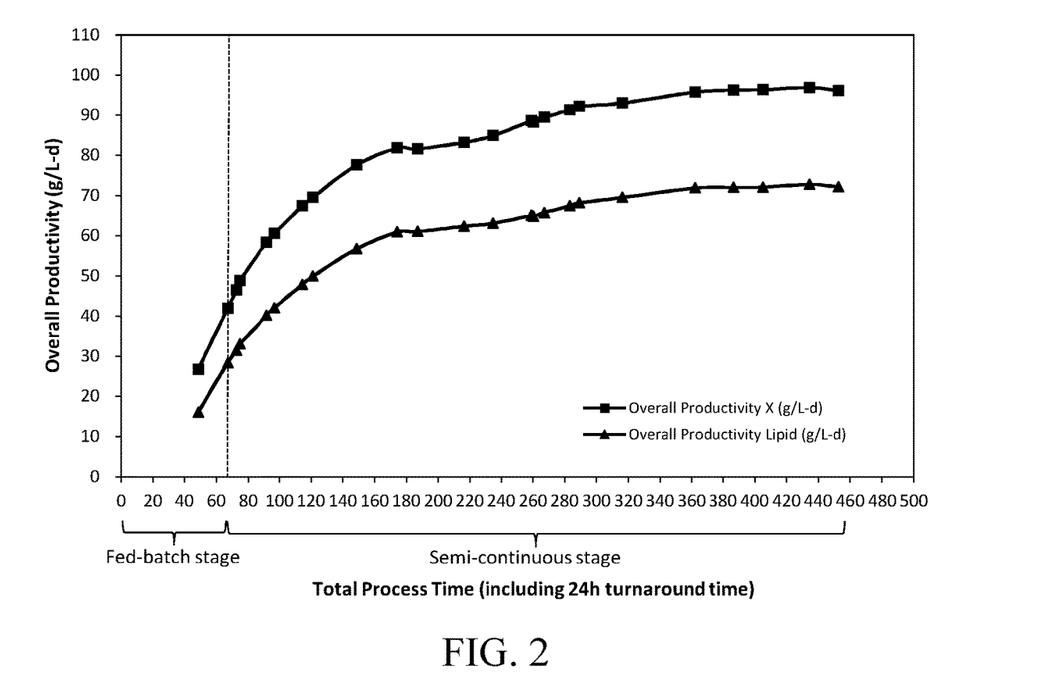
FIG. 2 is a graph showing the overall biomass (■) and oil productivity (▲) of ONC-T18 grown under semi-continuous conditions. The high productivity values shown in FIG. 2 far exceeded the achievable value under typical batch or fed-batch process.

The provided semi-continuous process extends the growth and oil production at the culture's peak productivity level. Assuming a 24-hour turnaround time to be included to the total process time, the overall biomass (X) productivity at any given time point of the process can be calculated as: X (gram)/Culture Volume (liter)/Time (hour)×24 (hours/day) with the final unit being g/L-day. The overall oil productivity at any given time point can be similarly calculated as: Oil (gram)/Culture Volume (liter)/Time (hour)×24 (hours/day). As seen in the overall plot of the biomass and oil productivity, at the end of a typical fed-batch process (indicated by the dividing line at 67 hours), the biomass and oil productivity are only 42 g/L-d and 28 g/L-d, respectively (FIG. 2). By extending the fermentation under the provided semi-continuous mode to 453 hours (19 days), the overall biomass and oil productivity gradually increased and reached a plateau of 96 g/L-d and 72 g/L-d, respectively (FIG. 2). These high productivity values far exceeded the achievable value under typical batch or fed-batch processes.

Briefly, ONC-T18 cells were first grown using a fed-batch fermentation process to high cell concentration and high oil content, at which point the predefined nitrogen source has been exhausted in the medium, the carbon source is controlled at close to zero level, and the instantaneous volumetric biomass/oil productivity are within their maximum region. A certain volume of the culture broth was harvested (10%), and the same volume of fresh medium containing a predefined concentration of carbon and nitrogen nutrients as well as all other necessary mineral nutrients was added to the fermenter to replace the harvested broth. The carbon and nitrogen in the feeding medium also need to be at a certain ratio in order to obtain and maintain high oil content in the culture. For FIG. 2, glucose and ammonium sulfate ((NH4)2SO4) concentrations of 300 g/L and 7.5 g/L, respectively, were used in the feeding medium corresponding to carbon (C) to nitrogen (N) ratio of 88:1 (molar ratio). The cultivation continues with the culture developing some more biomass and oil using the newly provided medium. Once the carbon source has been depleted, the partial broth harvest and fresh medium supply cycle was repeated. Using such a process, high density biomass containing high oil content can be produced and harvested in a semi-continuous manner, and the total duration of the process can be much longer than any batch or fed-batch mode of cultivation of such microorganisms.

Figure 3:
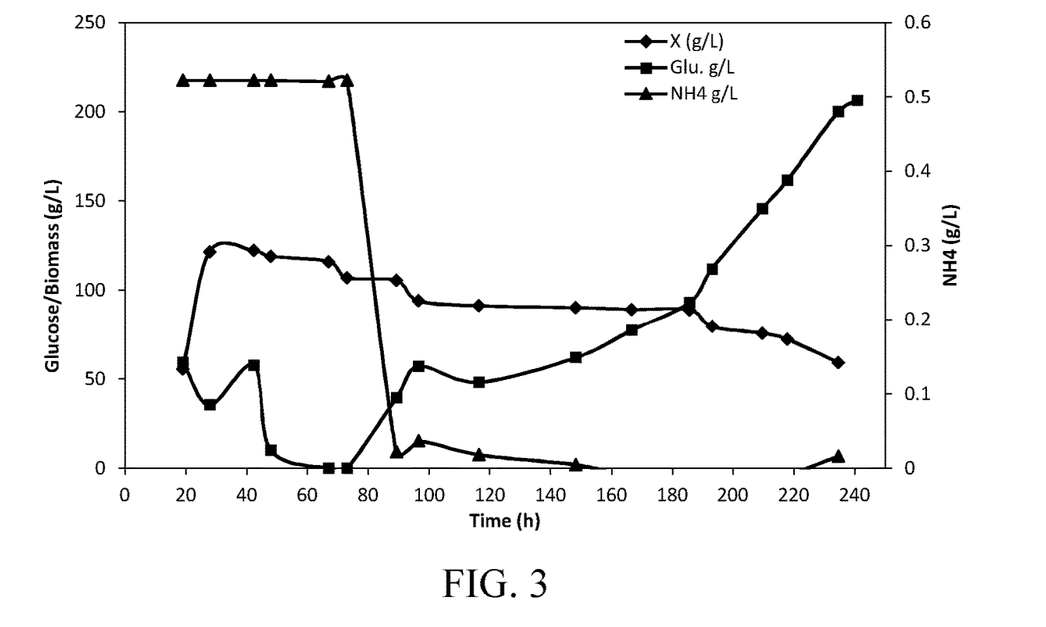
FIG. 3 is a graph showing the effects of continuous fermentation methods on ONC-T18. Continuous fermentation resulted in unsustainable fermentation, decrease in biomass and increase in glucose concentration in effluent. The fermentation was stopped due to line clogging.
Figure 4:
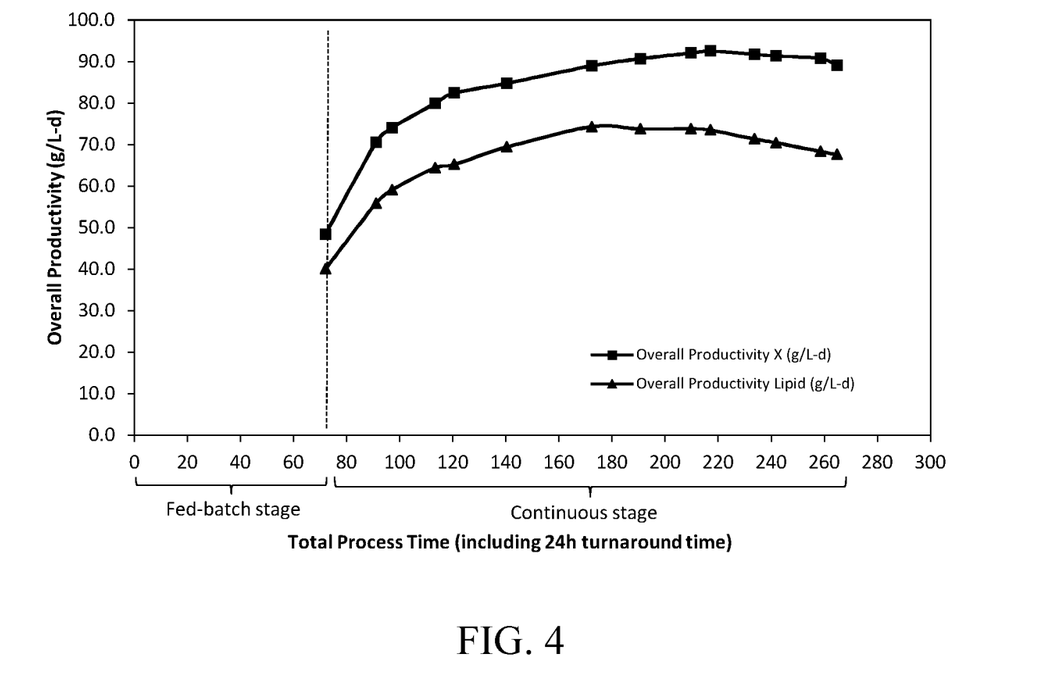
FIG. 4 is a graph showing the overall biomass (■) and oil productivity (▲) of ONC-T18 grown under continuous conditions. Continuous fermentation resulted in unsustainable fermentation and reduced biomass and oil productivity.
Figure 5:
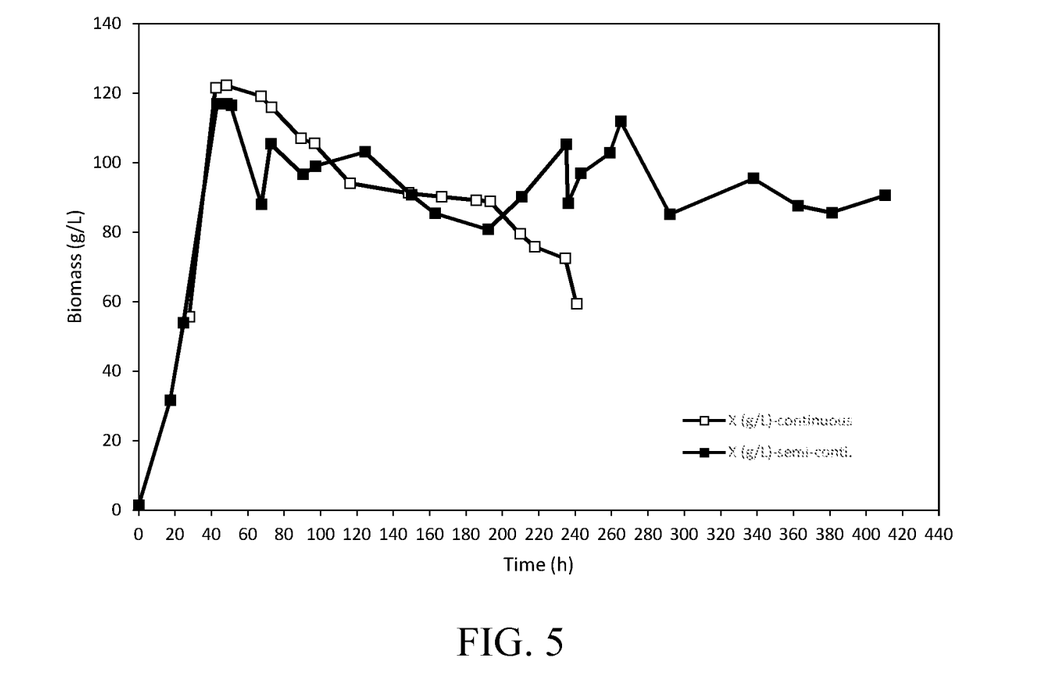
FIG. 5 is a graph showing the biomass productivity of ONC-T18 grown under semi-continuous and continuous fermentation. Semi-continuous fermentation resulted in prolonged biomass productivity.
Figure 6:
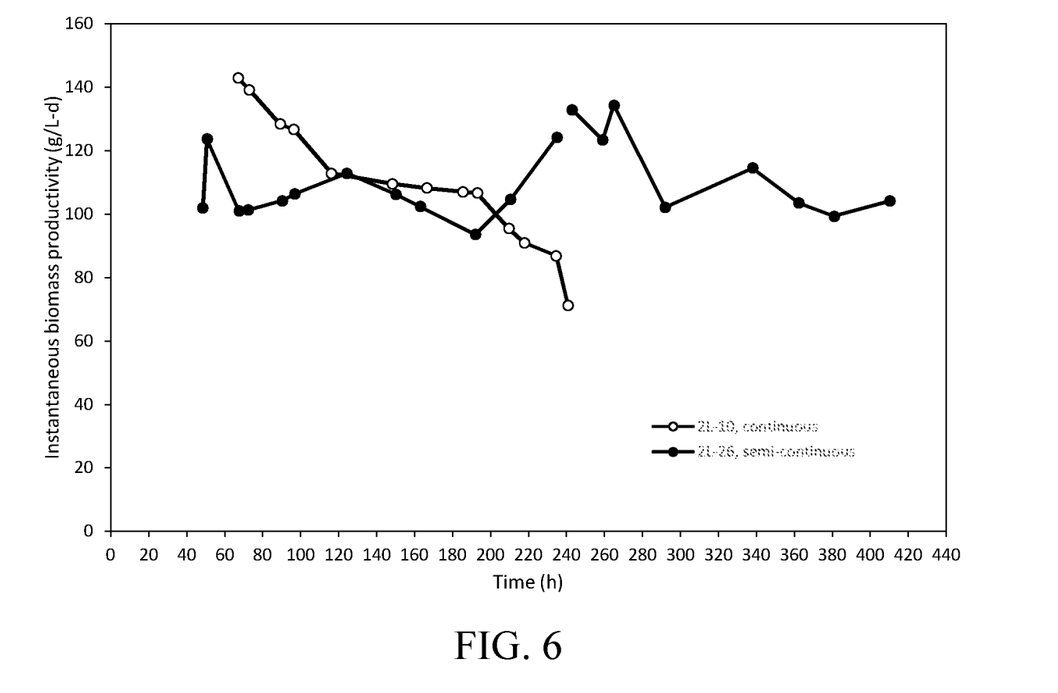
FIG. 6 is a graph showing the instantaneous biomass productivity (determined at the given time points) of ONC-T18 grown under continuous and semi-continuous fermentation conditions.
Figure 7:
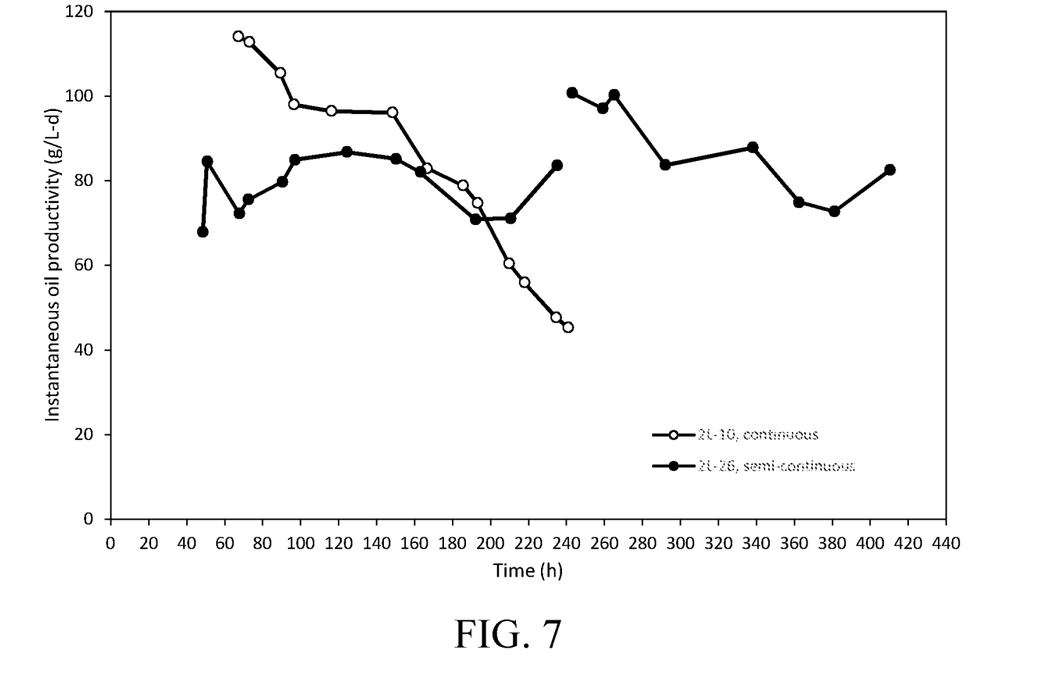
FIG. 7 is a graph showing the instantaneous oil productivity (determined at the given time points) of ONC-T18 grown under continuous and semi-continuous fermentation conditions.

To determine whether the provided semi-continuous method is better than continuous fermentation methods, cells were grown under continuous culture conditions using a C:N ratio of 88:1. The results are shown in FIGS. 3-7. Specifically, FIGS. 3 and 4 show continuous fermentation resulted in unsustainable fermentation, a decrease in biomass, and an increase in glucose concentration in effluent. The fermentation was stopped due to line clogging. FIGS. 5, 6, and 7 show comparisons of the biomass or oil productivity of ONC-T18 grown under semi-continuous and continuous fermentation conditions. Semi-continuous fermentation resulted in higher biomass and oil productivity and allowed for the culture to be maintained under high productivity conditions for a longer period of time. In fact, in this experiment, continuous fermentation method lasted approximately 160 hours less than semi-continuous fermentation.

What is claimed is:

1. A method of producing a biomass of oil-producing microorganisms comprising the steps of:
   (a) culturing the oil-producing microorganisms in a container with a medium comprising a first carbon to nitrogen ratio until the culture reaches a threshold indicator, wherein the threshold indicator is the concentration of carbon in the culture medium and wherein the concentration of carbon is at or near zero;
   (c) harvesting a 5% to 20% of the culture and maintaining the majority of the culture in the container; and
   (d) promoting production of the biomass of oil-producing microorganisms by adding fresh medium to the container at a volume of substantially the same volume as the harvested portion, wherein the fresh medium comprises a second carbon to nitrogen ratio.

2. The method of claim 1, wherein the first carbon to nitrogen ratio is from 30:1 to 60:1.

3. The method of claim 1, wherein the first carbon to nitrogen ratio is from 40:1 to 50:1.

4. The method of claim 1, wherein the second carbon to nitrogen ratio is from 70:1 to 95:1.

5. The method of claim 1, wherein the second carbon to nitrogen ratio is from 80:1 to 90:1.

6. The method of claim 1, wherein the portion harvested comprises 10% of the culture.

7. The method of claim 1, wherein the method further comprises monitoring optical density (OD), cell concentration, carbon dioxide production rate, pH, dissolved oxygen (DO), time, concentration of nitrogen in culture medium, biomass productivity, oil productivity, or any combination thereof.

8. The method of claim 1, comprising repeating the steps of (a)-(c).

9. The method of claim 1, further comprising isolating oil from the oil-producing microorganisms in the harvested culture.

10. The method of claim 1, wherein the culture is maintained at a biomass productivity comprising 60 g/L-d to 180 g/L-d.

11. The method of claim 10, wherein the culture is maintained at a biomass productivity comprising 80 g/L-d to 130 g/L-d.

12. The method of claim 11, wherein the culture is maintained at a biomass productivity comprising 90 g/L-d to 100 g/L-d.

13. The method of claim 1, wherein the culture is maintained at an oil productivity comprising 35 g/L-d to 130 g/L-d.

14. The method of claim 13, wherein the culture is maintained at an oil productivity comprising 60 g/L-d to 90 g/L-d.

15. The method of claim 14, wherein the culture is maintained at an oil productivity comprising 70 g/L-d to 80 g/L-d.

16. The method of claim 1, wherein the biomass comprises 60% to 85% oil.

17. The method of claim 16, wherein the biomass comprises 65% to 75% oil.

18. The method of claim 1, wherein the culture is maintained for a period of hours, days, weeks, or months.

19. The method of claim 18, wherein the culture is maintained for at least 150 to 500 hours.

20. The method of claim 18, wherein the culture is maintained for at least 250 hours.

* * * * *